United States Patent [19]

Pennystone

[11] Patent Number: 4,508,114

[45] Date of Patent: Apr. 2, 1985

[54] ANTI-RAPE DEVICE

[76] Inventor: Anna G. Pennystone, 8150 Reading Rd., Cincinnati, Ohio 45237

[21] Appl. No.: 530,418

[22] Filed: Sep. 8, 1983

[51] Int. Cl.³ .............................................. A61B 19/00
[52] U.S. Cl. ................................................. 128/138 R
[58] Field of Search .................... 128/138, 132 R, 157, 128/1 R

[56] References Cited

U.S. PATENT DOCUMENTS 4,332,243  6/1982  Gutnick ............................ 128/132 R

*Primary Examiner*—Stephen C. Pellegrino
*Attorney, Agent, or Firm*—Charles R. Wilson

[57] ABSTRACT

An anti-rape device is adapted to be worn in the vaginal cavity of a female. The device comprises a hollow housing with adhesive means on the interior of the housing to adhere to any rapist and an irritant-containing pouch positioned within the housing which ruptures upon forceful contact with the rapist. The adhesive means ensures the device will adhere to the rapist thereby causing continued discomfort.

10 Claims, 2 Drawing Figures

ANTI-RAPE DEVICE

The present invention relates to an improved anti-rape device. More particularly, the invention relates to a device which is adapted to be inserted into the vaginal cavity of a human female for protection against a rapist.

Rape is a crime which everyone is aware of and feels is repugnant to society. It is a crime which is and has been prevalent throughout society. Through the years, various measures have been suggested for preventing a rape. An obvious means of preventing rape by the use of a physical force greater than that possessed by the attacker has not met with success. Thus, weapons e.g. knives, guns, aerosol sprays and various other types of physical force can be used by the female. Unfortunately, the male attacker is often stronger which, together with the element of surprise, will prevent the victim from using the weapon. Self-defense techniques have also been found to be deficient. This is not only because they require a high level of skill and physical conditioning to be effective but also they require a violent mental attitude to effectivly repulse an attacker. While various types of whistles and alarms that are intended to summons assistance are available on the market and can be effective, they are not the entire answer to the problem. This is because of the element of surprise and the lack of time within which to use the whistle or alarm.

Devices which can be termed as passive prevention devices have also been avocated for use by the female. For example, the use of an armour undergarment which can be locked in place to eliminate the possibility of rape has been suggested. Other devices have been advocated to be worn in the vaginal cavity of the female. These devices are illustrated in U.S. Pat. Nos. 4,016,875; 4,167,183 and 4,237,876. The devices illustrated in these three patents all involve the use of a vaginal insert which contains a needle or a sharp razor blade which will injure the rapist upon penetration into the female. While such devices undoubtedly will repulse an rape attack, they can result in additional physical violence being inflicted upon the female. For this reason the devices described in the prior art may do more harm than good.

SUMMARY OF THE INVENTION

The present invention relates to an anti-rape device adapted to be worn in the vaginal cavity of the human female. The device comprises a hollow housing dimensioned to be received within the vaginal cavity. The housing is closed at one end and open at the other end. An irritant-containing pouch is positioned within the housing. The pouch is made of material which will rupture upon forceful contact with the penis of the rapist, thereby releasing its contents. Adhesive means are also provided on the inside walls of the hollow housing for securely affixing the device to the rapist to ensure prolonged discomfort and concern only for his own well-being.

DETAILED DESCRIPTION OF THE INVENTION

Figure 1:
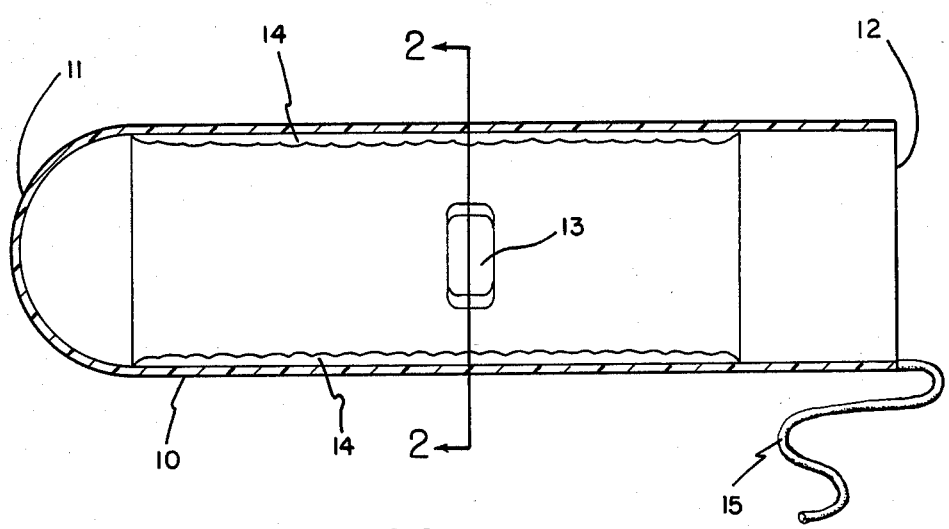
FIG. 1 is a side view partially in section of the anti-rape device of this invention.
Figure 2:
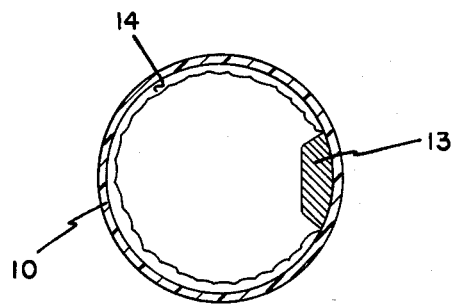
FIG. 2 is a cross-sectional view of the device of FIG. 1 taken along lines 2—2.

Referring to FIGS. 1 and 2 an anti-rape device is shown which comprises a hollow housing 10 dimensioned to be releasably received with the vaginal of the human female. The hollow housing is typically tubular in shape and ranges from about two inches to about five inches in length. The housing is closed at end 11 and open at end 12. The closed end will normally be hemispheric in shape for ease of manufacture and insertion by the user. The housing is preferably semipliable, but rigid enough not to collapse upon itself. It can be made of rubber or a synthetic elastomeric material.

Positioned within the hollow housing is an irritant-containing pouch 13. Preferably, the pouch is positioned about mid-way between the ends of the hollow housing, either mounted on the housing's wall, circling the wall as in the form of a ring or suspended in the center of the housing be suitable means. The irritant contained within the pouch is a material which when it contacts the penis of a rapist will be immediately felt and the pain associated there will be such as to cause the rapist to terminate his attack and to withdraw. The irritant can be any quick acting material which is an irritant to human skin. Acids such as formic acid, hydrocloric acid or other known acids can be used. The pouch which contains the irritant must be of a material that will rupture upon forceful contact but at the same time must be sufficiently strong to contain the irritant during normal use and be impermeable to the irritant. A thin rubber or synthetic elastomeric material is sufficient.

Adhesive means 14 also associated with the interior of the hollow housing will cause the anti-rape device to remain on the rapist. The adhesive means used on the inside walls of the hollow housing can be a liquid or semi-solid material such as a glue or a two-sided adhesive tape. Several different adhesives and adhesive tapes are known which can be used in the device of this invention. The adhesive must be such that it readily adheres to human skin and not be easily removed. Of course, when the anti-rape device is being worn, the adhesive must be in a tacky state. Such a state may be its normal state or body heat supplied by the female could render a normally non-tacky material tacky and thus suitable as an adhesive. The liquid or semi-solid adhesive can be spread on the interior walls of the housing as shown in FIG. 1. Alternatively, the adhesive can be contained within a rupturable pouch positioned within the housing. The pouch can be in any shape including ring-shaped so as to fit within the housing. In case of attack the adhesive ensures the continued action of the irritant on the rapist which preoccupies him with his own welfare and allows the female victim to escape. This is to be contrasted with the devices of the prior art where once the rapist has been injured, the cause of the injury is immediately removed. This allows the rapist to vent his anger on the victim without there being a further concern for this own immediate safety.

In a preferred embodiment of the invention string means 15 is attached to the hollow housing for easy removal of the device. Such string means have been used with tampons and are readily adapted for use with this invention. In another preferred embodiment the open end of the housing is provided with an elastic retaining ring for ease of insertion by the wearer and as a means for ensuring that the adhesive remains inside the housing.

In operation, it has been found that the anti-rape device of the present invention when properly designed and fitted can be worn comfortably and without danger during almost all normal activities. The device is easily inserted by the user. The device can be used on a simi-permanent basis or only occasionally depending on the desires of the user. During the course of a rape, the anti-rape device adheres to the rapist and at the same time the pouch containing the irritant ruptures. The irritant then contacts the rapist and causes great discomfort. This in effect terminates the rape attack. While the rapist is concerned with his own safety and welfare the victim will have time to escape or summons for help.

What is claimed is:

1. An anti-rape device adapted to be worn in the vaginal cavity of a human female, comprising:
   (a) a hollow housing dimensioned to be releasably received within the vagina, said housing being closed at one end and open at the other end; said housing being semi-pliable, but rigid enough not to collapse upon itself
   (b) adhesive means on the inside walls of the hollow housing for securely adhering to the penis of a rapist during penetration of a vagina containing the anti-rape device; and
   (c) an irritant-containing pouch positioned within the hollow housing, said pouch being made of a material which will rupture upon forceful contact with the rapist thereby releasing its contents.

2. The anti-rape device of claim 1 wherein the irritant is a skin irritant.

3. The anti-rape device of claim 2 wherein the irritant is an acid.

4. The anti-rape device of claim 3 wherein the acid is formic acid or hydrochloric acid.

5. The anti-rape device of claim 2 wherein the adhesive means is a liquid or semi-solid adhesive which is applied to the interior of the hollow housing.

6. The anti-rape device of claim 2 wherein the adhesive means is a two-sided adhesive tape affixed to the interior of the hollow housing.

7. The anti-rape device of claim 5 wherein the irritant-containing pouch is positioned about mid-way between the ends of the hollow housing.

8. The anti-rape device of claim 7 wherein the adhesive is contained within a rupturable pouch and mounted on the interior wall of the hollow housing.

9. The anti-rape device of claim 1 further comprising a string attached to the housing to facilitate removal of the device from the vaginal cavity.

10. The anti-rape device of claim 1 wherein the housing is made of a rubber or synthetic elastomeric material.

* * * * *